(12) United States Patent
Yee

(10) Patent No.: US 6,283,954 B1
(45) Date of Patent: Sep. 4, 2001

(54) LINEAR ARRAY EYE TRACKER

(75) Inventor: Kingman Yee, Sunnyvale, CA (US)

(73) Assignee: VISX, Incorporated, Santa Clara, CA (US)

( * ) Notice: Subject to any disclaimer, the term of this patent is extended or adjusted under 35 U.S.C. 154(b) by 61 days.

(21) Appl. No.: 09/365,428

(22) Filed: Aug. 2, 1999

Related U.S. Application Data

(63) Continuation-in-part of application No. 09/249,912, filed on Feb. 12, 1999, now abandoned, which is a continuation of application No. 09/063,879, filed on Apr. 21, 1998, now Pat. No. 5,966,197.

(51) Int. Cl.⁷ ........................................................ A61B 3/14
(52) U.S. Cl. ............................... 606/5; 351/212; 351/210
(58) Field of Search ..................................... 351/205, 206, 351/209, 210, 211, 212; 606/2, 4, 5, 13, 12; 607/88, 89

(56) References Cited

U.S. PATENT DOCUMENTS

| | | |
|---|---|---|
| 3,804,496 | 4/1974 | Crane et al. . |
| 4,169,663 | 10/1979 | Murr . |
| 4,421,486 | 12/1983 | Baldwin et al. . |
| 4,443,075 | 4/1984 | Crane . |
| 4,579,430 | 4/1986 | Bille . |
| 4,669,466 | 6/1987 | L'Esperance . |
| 4,836,670 | 6/1989 | Hutchinson . |
| 4,848,340 | 7/1989 | Bille et al. . |
| 4,852,988 | 8/1989 | Velez et al. . |
| 4,950,069 | 8/1990 | Hutchinson . |
| 4,973,149 | 11/1990 | Hutchinson . |
| 5,016,643 | 5/1991 | Applegate et al. . |
| 5,098,426 | 3/1992 | Sklar et al. . |
| 5,162,641 | 11/1992 | Fountain . |
| 5,231,674 | 7/1993 | Cleveland et al. . |
| 5,270,748 | 12/1993 | Katz . |
| 5,345,281 | 9/1994 | Taboada et al. . |
| 5,360,424 | 11/1994 | Klopotek . |
| 5,410,376 | 4/1995 | Cornsweet et al. . |
| 5,430,505 | 7/1995 | Katz . |

(List continued on next page.)

FOREIGN PATENT DOCUMENTS

| | | | |
|---|---|---|---|
| WO 94/18883 | 9/1994 | (WO) . | |
| WO 95/27453 | 10/1995 | (WO) . | |
| WO 99/12467 | 3/1999 | (WO) . | |
| WO 99/20173 | 4/1999 | (WO) . | |
| WO 99/23936 | 5/1999 | (WO) . | |
| WO 99/55216 | 11/1999 | (WO) . | |
| WO 00/09002 | 2/2000 | (WO) | ................................ A61B/3/02 |
| WO 00/13628 | 3/2000 | (WO) | ................................ A61B/9/01 |

OTHER PUBLICATIONS

Rashbass et al., "New Method for Recording Eye Movement", *Journal of the Optical Society of America* (1960) 50(7):642–644.

Crane et al., "Generation–V Dual Purkinje–Image Eyetracker", *Applied Optics* (1985) 24(4):527–537.

Young & Sheena, *Behavior Research Methods and Instrumentation* (1975) vol. 7, No. 5, Survey of eye movement recording methods, pp. 401–429.

*Primary Examiner*—George Manuel
(74) *Attorney, Agent, or Firm*—Townsend Townsend & Crew LLP; Mark D. Barrish, Esq.

(57) ABSTRACT

Improved devices, systems, and methods for sensing and tracking the position of an eye make use of the contrast between the sclera and iris to derive eye position. In many embodiments, linear photodetectors extend across the pupil, optionally also extending across the iris to the sclera. A pair of such linear photodetectors can accurately sense and measure one-dimensional positioning error and provide feedback to a one-dimensional positioning apparatus, resulting in a simple, highly linear system capable of accurate position tracking.

10 Claims, 4 Drawing Sheets

U.S. PATENT DOCUMENTS

| | | |
|---|---|---|
| 5,471,542 | 11/1995 | Ragland . |
| 5,474,548 | 12/1995 | Knopp et al. . |
| 5,572,596 | 11/1996 | Wildes et al. . |
| 5,604,818 | 2/1997 | Saitou et al. . |
| 5,620,436 | 4/1997 | Lang et al. . |
| 5,632,742 | 5/1997 | Frey et al. . |
| 5,752,950 | 5/1998 | Frey et al. . |
| 5,782,822 | 7/1998 | Telfair et al. . |
| 5,928,221 * | 7/1999 | Sasnett et al. .............................. 606/5 |
| 6,022,108 | 2/2000 | Yoshida et al. ........................ 351/208 |
| 6,027,216 | 2/2000 | Guyton et al. ......................... 351/200 |
| 6,027,494 | 2/2000 | Frey ......................................... 606/5 |
| 6,030,376 | 2/2000 | Arishima et al. .......................... 606/4 |

\* cited by examiner

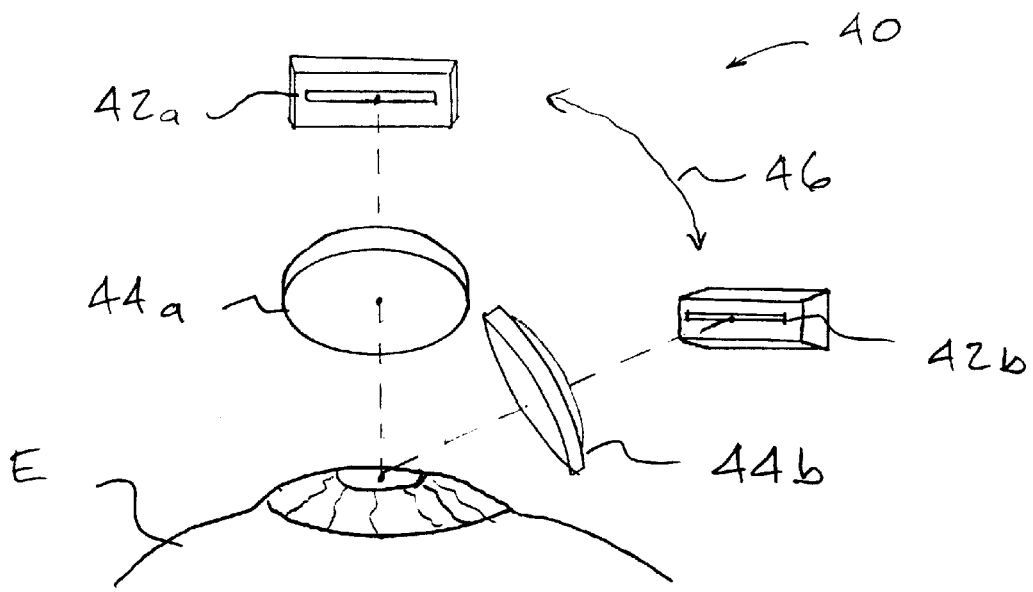
FIG. 6
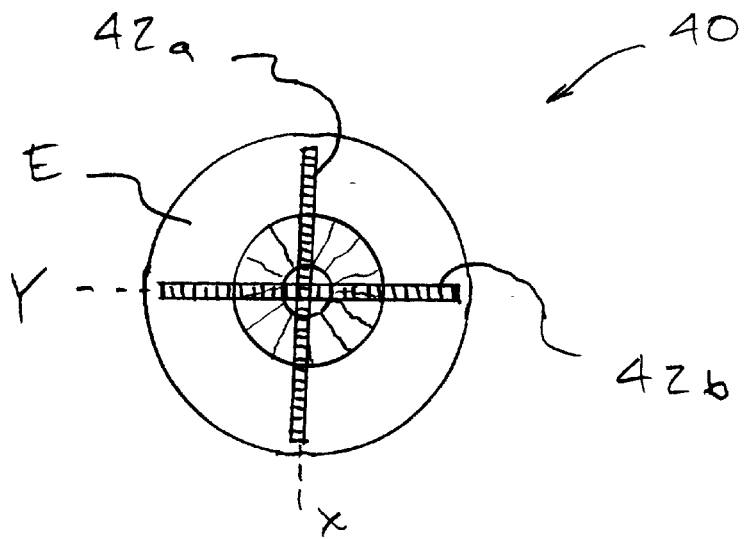
FIG_7

LINEAR ARRAY EYE TRACKER

CROSS REFERENCE TO RELATED APPLICATIONS

This application is a continuation-in-part of, and claims the benefit of U.S. patent application Ser. No. 09/249,912, filed Feb. 12, 1999, now abandoned; which is a continuation application of U.S. patent application Ser. No. 09/063,879, filed Apr. 21, 1998, now U.S. Pat No. 5,966,197 the full disclosures of which are incorporated herein by reference.

BACKGROUND OF THE INVENTION

FIELD OF THE INVENTION

The present invention is generally concerned with ophthalmic instruments and surgery, and more particularly relates to systems, methods, and apparatus for sensing and/or tracking the position of a human eye. The present invention is particularly useful for tracking the position of the eye during laser eye surgery, such as photorefractive keratectomy (PRK), phototherapeutic keratectomy (PTK), laser in situ keratomileusis (LASIK), or the like. In an exemplary embodiment, the present invention is incorporated into a laser ablation system to modify the distribution of laser energy directed at the cornea based on the sensed position of the eye during the laser ablation procedure.

The ability to track or follow the movement of a patient's tissue is recognized as a highly desirable feature, particularly for use in laser delivery systems designed to effect precision surgery in delicate ocular tissue. The eye movements to be tracked include not only the voluntary movements (which can be damped with specialized treatment), but also the involuntary movements which are more difficult to control in a living patient. In other words, even when the patient is holding "steady" fixation on a visual target, eye movement still occurs. This involuntary motion may compromise the efficacy of some ocular surgical procedures, which generally require a rate of precision. In fact, such involuntary movements may occur despite the "total immobilization" of the eye, as such techniques are not fully effective in suppressing involuntary eye motion, and are also rather uncomfortable for the patient. Automatic tracking of the eye may alleviate any need for this uncomfortable immobilization, and may offer a method for more effectively accommodating differing types of eye motion. In other words, augmenting surgery with real time eye tracking may improve the accuracy and speed with which known laser eye surgery can be performed, and may also enable new procedures to be carried out for the first time.

A variety of techniques have been described for tracking eye movements. One general type of eye tracking technique has been called "optical point tracking." Optical point trackers utilize various lens-like properties of the eye to locate optically distinguishable locations (for example, the first, second, third, and fourth Purkinje points). Unfortunately, such optical point trackers implicitly assume that the eye moves as a rigid body. As the eye actually flexes during movement, transient relative motions of lens structure can lead to fictitious optical point position information. In addition, optical point tracking systems are rather complex, and may exhibit large variability between individuals.

Another class of eye tracking techniques generally involve digital pattern recognition. These digital techniques generally require very fast frame-rate CCD cameras and sophisticated processing algorithms. As tracking frequency response is considerably slower than update frequency, they tend to be relatively slow. Hence, these known digital methods generally require extremely fast repositioning mechanisms to leave time for complex electronic processing within an acceptable total response time.

A recent promising technique for tracking eye movements takes advantage of the difference in the light scattering properties of the iris and sclera. In this technique, light is projected on to the iris/sclera interface or limbus, and the scattered light is detected by photodetectors to determine the boundary location. The relative position of this boundary can then be monitored to track the position of the eye.

Unfortunately, the limbus is more a transition zone between the cornea and the sclera, rather than a sharp boundary. As a result, techniques which rely on edge detection may lack the desired accuracy, and may not be capable of tracking large amplitude movements of the eye. Another disadvantage of known limbus tracking techniques is the relative complexity of signal processing required to effect tracking. In other words, when the eye moves so that the limbus is no longer in the nominal position, effecting realignment using known tracking systems requires fairly complex manipulations of the photodetector signal to properly instruct the repositioning system. These complex signal manipulations increase overall system complexity, and also slow the system down. Work in connection with the present invention indicates that slow tracking system response and less than desirable accuracies may in-part be the result of tracking system non-linearities. While adequate tracking response may be possible using known "pin-point" limbus trackers with accurately aligned photodetectors disposed precisely along the edge of the iris/sclera interface, providing and/or maintaining such alignment adds additional system components and complexity, particularly in light of the variability of eye geometry between differing patients.

In light of the above, it would be desirable to provide improved eye sensing and tracking devices, systems, and methods. It would be particularly desirable if these enhanced techniques improved tracking response times and sensitivity, but without significant increases in cost or complexity of the tracking mechanism. It would be particularly desirable to provide these enhanced capabilities in a system which was adaptable for use in laser eye surgery for accurately sensing and/or tracking a variety of patient eye movements.

SUMMARY OF THE INVENTION

The present invention provides improved devices, systems, and methods for tracking the position of an eye. The techniques of the present invention generally make use of the difference in contrast between features of the eye (such as between the white of the eye or sclera and the colored iris, or between the iris and the pupil) to derive the position of the eye. In many embodiments, linear photodetectors having an elongate sensing area extend from one feature to another across the contrast border. Where the eye is positioned between a pair of such linear photodetectors, movement of the eye from one linear detector toward the other linear detector will change the relative amounts of light striking each linear detector. The amount of misalignment between the linear detectors and the eye will be proportional to the difference in the signal output by the detectors. Therefore, this difference in signal between a pair of opposed linear photodetectors provides an excellent feedback signal, requiring only very simple amplification for use as an input signal for a repositioning mechanism. Such simple signal processing not only reduces the circuitry complexity and cost, but significantly enhances the speed and accuracy of tracking.

Conveniently, linear photodetectors can accurately sense and measure one-dimensional positioning error of a substantially round feature such as the iris or pupil. The tracking systems of the present invention often take advantage of this one-dimensional error measurement by measuring light along two axial segments which cross the contrast border and each other. This arrangement can provide accurate relative position information despite the lack of a sharp contrast boundary, such as when using the gradual contrast boundary often found at the limbus.

In a first aspect, the invention provides a laser eye surgery system for effecting a desired change in optical characteristics of an eye during lateral movements of the eye in X and Y orientations. The eye has a first feature and a second feature with a contrast border therebetween. The system comprises a first linear photodetector having an elongate detector area. The detector area of the first linear photodetector is oriented to receive light from the first and second feature of the eye along a first axis extending across the contrast border. A second linear photodetector has an elongate detector area which is oriented to receive a light from the first and second feature of the eye along a second axis extending across the contrast border. The second axis is disposed at an angle relative to the first axis. A processor is coupled to the first and second linear photodetectors. The processor calculates the lateral movement of the eye in the X and Y orientations in response to the light received from along the first and second axes. A laser is coupled to the processor. The laser directs a laser beam toward the eye to effect the desired change in optical characteristics of the eye. The beam moves laterally in response to the calculated lateral movements of the eye.

The first and second linear detectors will often sense light from elongate areas of the eye which are at substantially perpendicular orientations relative to each other, although oblique angle alignments may also be used. Optionally, each linear detector may produce a signal indicating total light received within the elongate detector area. Alternatively, each linear detector may comprise a linear array of light sensors, so that each linear detector produces a signal indicating an alignment of the contrast border along the light sensors. When measuring the location of a round feature such as the iris or pupil, such sensors might indicate the axial position of the round feature by determining the axial location of, for example, a low light measurement region along the array. Alternatively, the array may be analyzed as two separate sets of sensors by comparing the total light received from the sensors on one side of the array to the total light from sensors on the other side of the array.

The system will often include imaging optics associated with the first and second linear photodetectors. Such imaging optics can independently image the light from the eye on to the first and second linear photodetectors. This allows, for example, imaging of crossing axial segments on to the two photodetectors, with the axial segments preferably crossing within a pupil of the eye. The optics may be disposed off the optical axis of the eye, preferably offset from the optical axis by 90° so as to isolate X and Y lateral movements of the eye. In general, tracking system complexity and response time can be improved by independently coupling the first and second linear detectors to first and second beam scanning actuation systems, with each actuation system maintaining alignment between the linear detector and the eye along the sensing axis of the associated linear detector.

In another aspect, the invention provides a laser eye surgery method comprising illuminating a first feature and a second feature of an eye. Light is measured from the illuminated eye with a plurality of linear photodetectors while each linear detector is aligned to receive light from adjacent the first feature, from the second feature, and from across a contrast border therebetween. A lateral movement of the eye is determined from the measured light. A laser beam is directed toward a corneal tissue of the eye to effect a desired change in optical characteristics of the eye. The beam moves laterally in response to the determined lateral movements of the eye.

In the exemplary embodiment, the light from the illuminated eye is imaged independently by imaging optics so that first and second axial segments of the eye are imaged on to the first and second linear photodetectors, respectively. Ideally, the first and second axial segments cross within a pupil of the eye, the contrast border comprising the pupil/iris boundary and/or the limbus.

BRIEF DESCRIPTION OF THE DRAWINGS

FIGS. 6 and 7 schematically illustrate alternative linear photodetector arrangements in which imaging optics independently image the eye toward digital linear photodetectors so as to sense light from perpendicular axial segments which cross within the pupil of the eye.

DESCRIPTION OF THE SPECIFIC EMBODIMENTS

The present invention is directed to devices, methods, and systems for sensing and/or tracking the position of an eye in a living body. The techniques of the present invention generally make use of the contrast of a recognizable large scale boundary of the eye, such as at the cornea/sclera interface (the limbus). The sensing or tracking systems may optionally determine the location and velocity of these boundaries without having to resort to digital sampling techniques. In a preferred aspect, the cornea/sclera interface position is tracked relative to a specific axis using a pair of elongate photodetectors. By arranging these elongate detectors so that each extends across the relatively dark iris and beyond the limbus to the white sclera, the relative position of the limbus (and the pupil) can be determined.

The present invention optionally makes use of linear bulk photodetectors. These photodetectors are capable of providing a signal which indicates a total illumination along an elongate light sensing area To take advantage of the significant contrast between the sclera and iris, without having to pinpoint and track a position of a boundary between these large, high contrast structures, the light sensing area will extend across (and beyond) the limbus.

The devices, systems, and methods of the present invention may find application in a variety of settings. For example, the eye position sensing techniques of the present invention may be used for clinical or academic studies of both saccadic and voluntary eye movements. These techniques and structures will find their most immediate application in augmenting laser eye surgery. More specifically, the tracking systems of the present invention may be used to maintain alignment between a therapeutic laser beam and an eye to enhance the accuracy of laser eye surgery directed at reshaping of the cornea. Alternatively, the pairs of linear photodetectors may be used without tracking to interrupt such a laser photoablation procedure whenever the eye moves beyond an acceptable aligned range. Regardless, the paired linear bulk photodetectors of the sensing/tracking system of the present invention offer enhanced system response times over a broad range of eye motion amplitudes.

Figure 1:
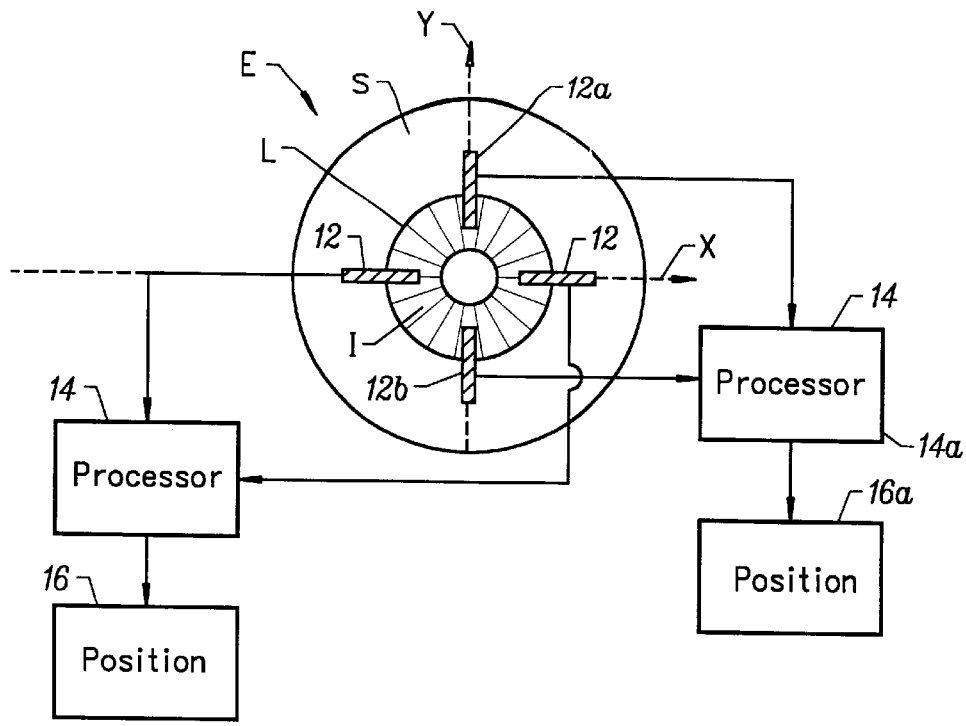
FIG. 1 schematically illustrates the tracking system of the present invention, in which lateral movements of the eye are measured from the difference in light intensity measured between two pairs of bulk linear photodetectors along two independent measurement/repositioning axes.

Referring now to FIG. 1, a tracking system 10 is used to track lateral movements of an eye E using a series of linear bulk photodetectors 12. Detectors 12 are arranged in coaxial pairs, with signals from the detectors compared by a processor 14, the processor manipulating the detector signals to direct a repositioning mechanism 16. Repositioning system 16 will then alter alignment between eye E and detectors 12 based on the signals from the processor.

Detectors 12 each have an elongate light sensing area, the detectors generally being radially oriented. While detectors 12 are illustrated superimposed on eye E in the schematic of FIG. 1, it should be understood that the detectors will often sense a position of eye E based on an image of the eye. Hence, descriptions of the relative positions of detectors 12 relative to the structures and features of eye E will often, in practice, be carried out using an image of the eye. For example, eye E includes a sclera S and an iris I with a limbus L defining the border therebetween. Photodiodes 12 are disposed "across" limbus L to extend from iris I to sclera S, so that each bulk detector measures light from both the substantially white, relatively bright sclera, and from the much darker iris. However, it should be understood that the detector structures may be at some distance from the eye, so that the detectors actually extend across an image of the eye. The image of the eye will often be produced by an optical train between the eye and the detectors. Alternatively, the photodiodes may be mounted on a spectacle frame near the eye and oriented directly across the sclera/iris interface.

Linear detectors 12 will typically comprise elongate silicon photodiodes. Silicon photodiodes typically have time constants of tens of picoseconds. As a result, the sampling rate will often be limited by the exposure time. More specifically, sampling rate is inversely related to exposure time, so that the shorter the exposure time, the higher the sampling rate.

The spectral response for silicon photodiodes centers in the near infrared (typically around about 750 $\mu$m). These detectors are generally sensitive to light throughout a fairly broad spectrum, providing at least about fifty percent sensitivity throughout the range from 450 $\mu$m to 950 $\mu$m. The preferred illumination source will ideally include a significant output within this range when silicon photodiode detectors are used. Alternatively, detectors 12 may sense light anywhere throughout the range of about 350 to 1100 $\mu$m, either by making use of lower sensitivities, using alternative diode structures, or the like.

Figure 1A:
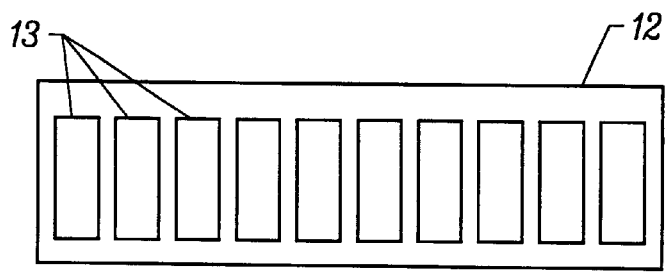
FIG. 1A schematically illustrates a photodiode structure for use in the system of FIG. 1.
Figure 5:
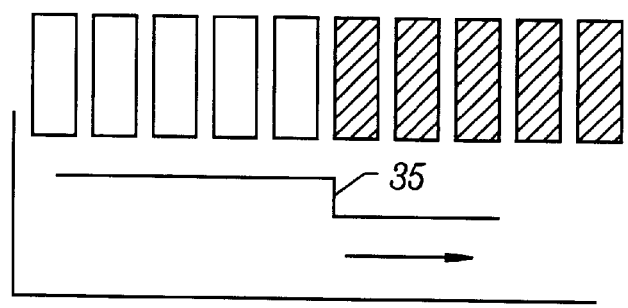
FIG. 5 schematically illustrates a method for measuring velocities using linear photodetectors.

An exemplary silicon photodiode structure is illustrated in FIG. 1A. Linear detector 12 includes an array of detector elements 13. Detector elements 13 are wider laterally (relative to the detector axis) than their axial length. This increases the overall detection area while preserving axial resolution. Hence, this structure provides increased axial signal to noise performance at the expense of resolution along an unused transverse sensing orientation.

Processors 14 will generally compare the signals produced by a pair of opposed detectors 12. The detectors will be long enough to measure lateral movements of eye E along one dimension, and will be much longer than their width. Processor 14a measures a position of iris I of eye E along an axis Y by comparing a signal produced by a first detector 12a to the signal produced by a second detector 12b. When eye E moves upward, the amount of sclera S adjacent first detector 12a will decrease, while the amount of the sclera adjacent the second detector 12b will increase. Conversely, the darker iris will increasingly be exposed to first detector 12a, and will have a decreasing exposure to second detector 12b. As a result, the total illumination signal produced by first detector 12a will decrease, while the signal produced by the second detector 12b will increase. By comparing these signals, processor 14a can sense that eye E has moved in the positive Y direction, and can also measure the amount and velocity of that movement based on the quantitative difference in signals, and by the rate of change of this difference, respectively.

Processors 14 may optionally comprise relatively simple analog circuits, or may alternatively include one or more analog-to-digital converters coupled to a digital processor. Use of an analog circuit may be preferred to enhance system response, particularly when repositioning mechanism 16 is adapted for use with an analog input signal.

Repositioning mechanism 16 will generally effect realignment between detectors 12 and eye E based on the positioning signal from processor 14. To separate the one-dimensional feedback loops along X and Y axes as illustrated in FIG. 1, positioning mechanism 16a attached to processor 14a will preferably affect only the alignment along axis Y. A variety of mechanisms may be used to provide such one-dimensional repositioning. For example, repositioning mechanism 16a may translate the spectacle frame supporting detectors 12 along the axis. Alternatively, repositioning mechanism 16 may pivot a mirror to effect realignment between an image of eye E and detectors 12. Where processor 14 provides an analog signal to repositioning mechanism 16, the repositioning mechanism will often include an analog electromechanical actuator such as a voice coil motor, or the like. Where processor 14 provides a digital signal to the repositioning mechanism, digital electromechanical actuators, such as stepper motors, may instead be used.

Figure 2:
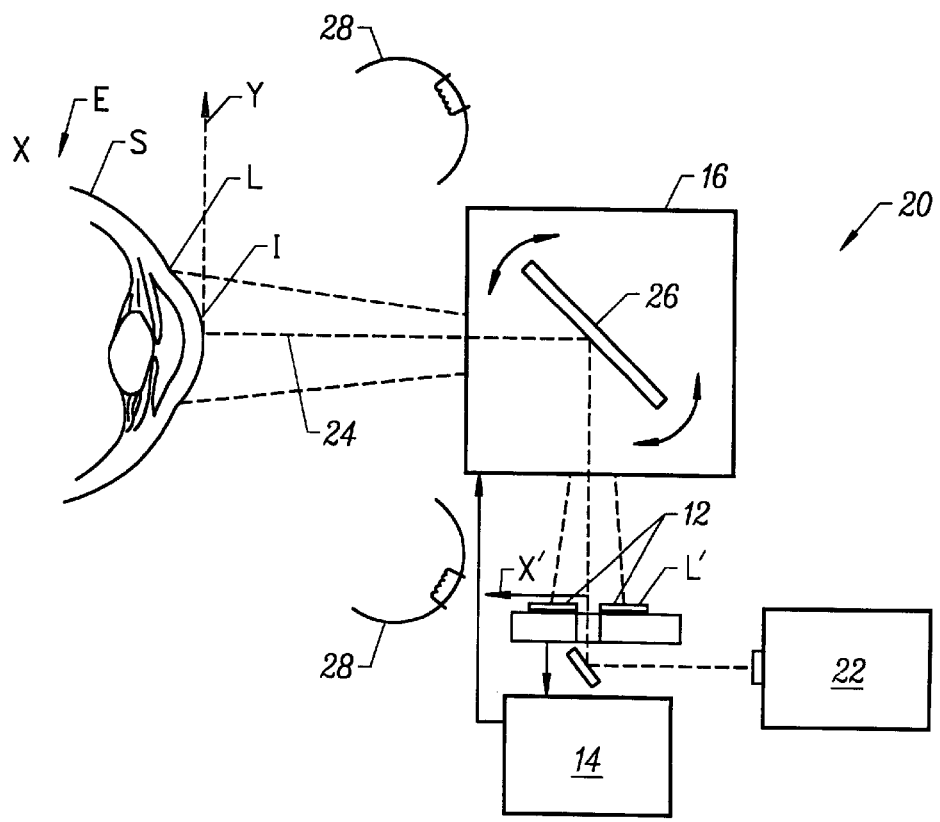
FIG. 2 is a schematic side-view of a laser surgery system including the tracking system of FIG. 1 for one of the two independent axes.

FIG. 2 illustrates a system 20 for selectively photoablating corneal tissues so as to effect reshaping of the cornea. Laser ablation system 20 incorporates the elements of tracking system 10 of FIG. 1. Laser ablation system 20 also includes a laser 22 which produces a laser beam 24. Laser beam 24 and linear detectors 12 are aligned relative to eye E by repositioning mechanism 16. In this embodiment, repositioning mechanism 16 makes use of a pivoting mirror 26 to alter a position of an image of eye E upon linear detectors 12. In other words, a limbus image L' superimposed on detectors 12 is aligned relative to the detectors by pivoting mirror 26 as shown. An optical train (not shown) may be included in positioning system 16 to image the eye, and to direct laser beam 24.

Imaging and sensing can be enhanced by illuminating eye E with light energy appropriate for measurement by detectors 12, as described above. Such illumination can be provided by oblique illuminators 28. The portions of tracking system illustrated in FIG. 2 will generally maintain alignment between laser beam 24 and eye E only along axis X. A second pair of detectors 12 coupled to an independent processor 14 and a substantially independent repositioning mechanism 16 can be used to track the eye during movements into and out of the plane of the drawing. An improved tracking system according to the invention using repositioning mirrors might be incorporated into a laser eye surgery system commercially available from VISX, Incorporated of Santa Clara, Calif., under the trademark STAR™ or STAR S2™.

Figure 3A:
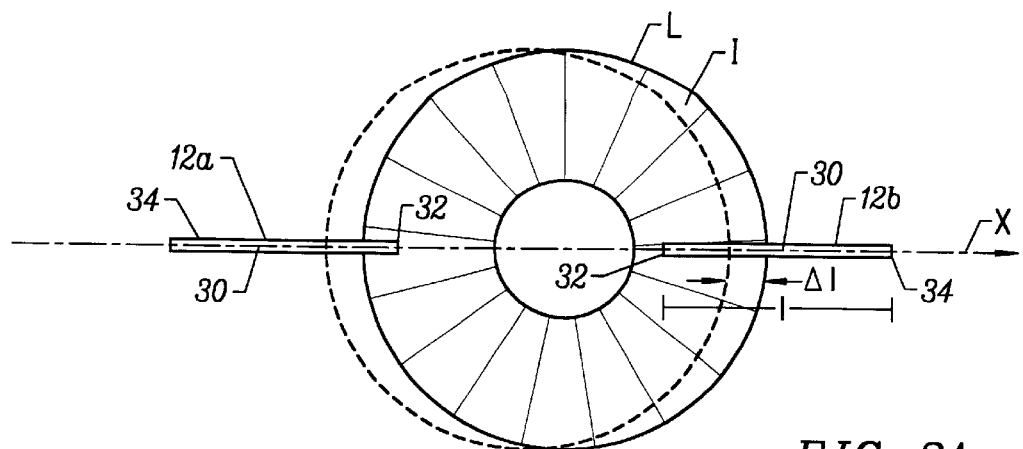
FIGS. 3A and 3B and 3C and 3D illustrate a method for sensing lateral eye movements in one-dimension using a pair of coaxial linear bulk photodetectors.
Figure 3B:
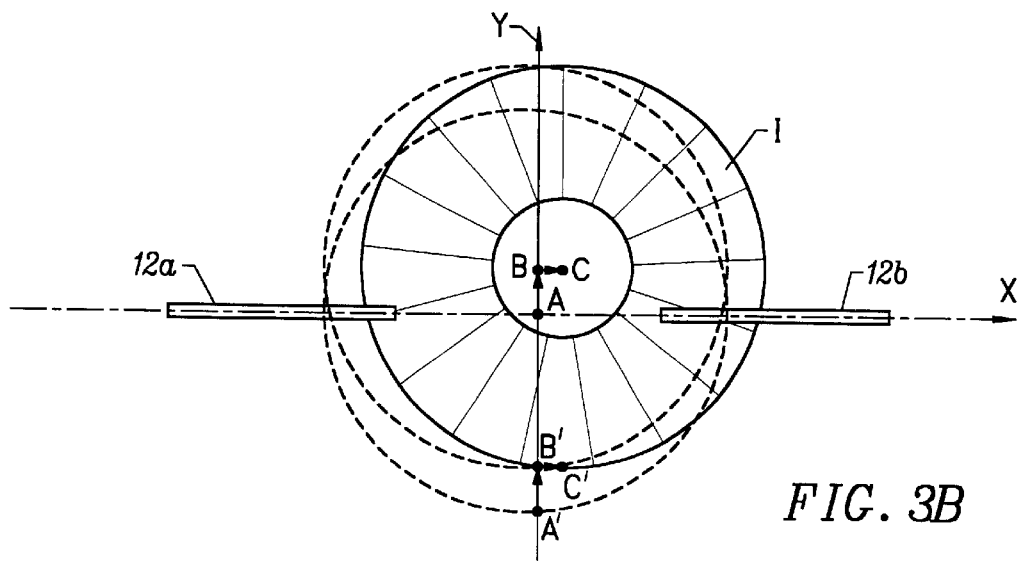

A change in relative signals from linear detectors 12 can be understood with reference to FIGS. 3A and 3B. Each of detectors 12 defines an elongate light sensing area 30 having an inner end 32 and an outer end 34. Inner ends 32 are generally aligned with iris I, while outer ends 34 extend out to the surrounding sclera. As a result, detectors 12 extend across limbus L and will sense a light in part from the relatively dark iris I, and in part from the significantly brighter sclera.

Detectors 12 will generally operate in pairs to sense the relative position of iris I. First detector 12a and second detector 12b are aligned coaxially along axis X. Qualitatively, when iris I moves to the right relative to detectors 12 (as illustrated in FIG. 3A, or when moving from point B to point C in FIG. 3B), more of the bright sclera is exposed to first detector 12a, thereby increasing its output signal. Conversely, more of second detector 12b is blanketed by the dark iris, thereby decreasing its signal. However, where iris I moves perpendicularly relative to axis X (such as from point A to point B as illustrated in FIG. 3B), the signal strength from both first detector 12a and second detector 12b will decrease by about the same amount. Hence, by comparing the signal from first detector 12a relative to the signal from second detector 12b, a pair of detectors can be used to indicate movement of iris I along axis X independently of any motion along a transverse axis Y.

Figure 3C:
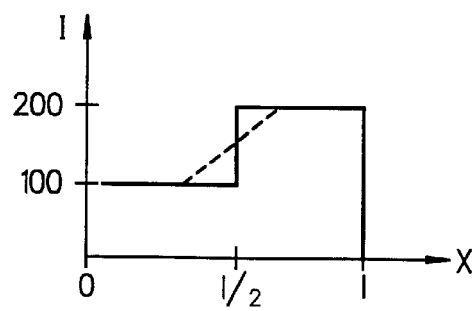

Quantitatively, the signal from second detector 12b (and for each of the detectors) will be:

$$S = \int_0^l I(x)\,dx$$

in which l is the length of second detector 12b, and I(x) is the intensity at a position x along length l. As an example, FIG. 3C illustrates an intensity profile comprising a step function with two different constant values: an arbitrary low intensity such as I=100 within iris I, and an arbitrary high intensity such as I=200 along the sclera. If we assume that half the length of second detector 12b is initially aligned with the iris and half is aligned with the sclera ($l_o$=l/2), the signal S is then given by:

$$s = \int_0^{l/2} I_1\,dx + \int_v^l 2I_2\,dx = \frac{1}{2}(I_1 + I_2)$$

Figure 3D:
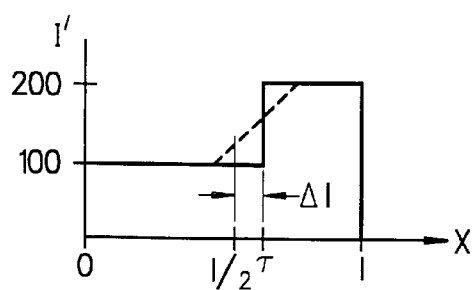

As described above, when iris I moves toward second detector 12b, signal S will decrease. More specifically, where iris I moves to the right by Δl so that the limbus moves from l/2 to l', the signal from second detector 12b will decrease by:

$$\Delta S = S - \int_o^r I_1\,dx + \int_r^l I_2\,dx$$
$$= \int_{lo}^r I_1\,dx - \int_{lo}^r I_2\,dx$$

in which l' is the new position of our theoretical limbus along second detector 12b (l'=$l_o$+Δl), while $I_1$ and $I_2$ are the intensities along the iris and sclera, respectively. Using our constant $I_1$ and $I_2$ from our step function example, we now have an intensity distribution I(x) as illustrated in FIG. 3D, giving us a total change in signal ΔS as follows:

$$\Delta S = (I_1 - I_2)\Delta l$$

in which ($I_1$-$I_2$) is the contrast between the iris and the sclera. (200–100=100 in our example).

Another way to think of the integral which gives us the signal S from our bulk photodetector is to look at it as a moving average of the light intensity along a slit. Advantageously, the tracking system compares the average light from slits which extend well beyond the gradual transition in contrast which actually occurs at limbus L, as illustrated by the broken line in FIGS. 3C and 3D. In contrast to the irregular variations along this transition, the average illumination through the opposed slits will vary smoothly when iris I moves relative to the detectors. For relatively small changes in alignment and relatively small contrast variations, the displacement is proportional to the change in signal.

Velocity measurements can be made quite accurately by monitoring a rate of change of the position along the X axis. The accuracy for such velocity measurements is a function of the ratio between the contrast and the noise from detectors 12. More specifically, velocities may be calculated as a rate of change of an edge signal 35, although the edge need not be sharp. A moment integral can be obtained from signal samples taken before a time interval and after the time interval. The difference in signal divided by the time interval will indicate velocity.

Good performance signal to noise (S/N) performance will provide a more accurate moment, thereby giving better velocity measurements. The better the S/N performance, the less likely a noise spike will be inadvertently interpreted as a movement of the eye. In other words, if there is too much noise, velocity measurements become difficult because the edge position becomes ill defined, and the moment will have a large standard error. Averaging of the data can help to improve the S/N performance to more accurately calculate a fixed or slow moving edge, but sequential signal averaging may reduce the maximum measurable velocity.

Figure 4:
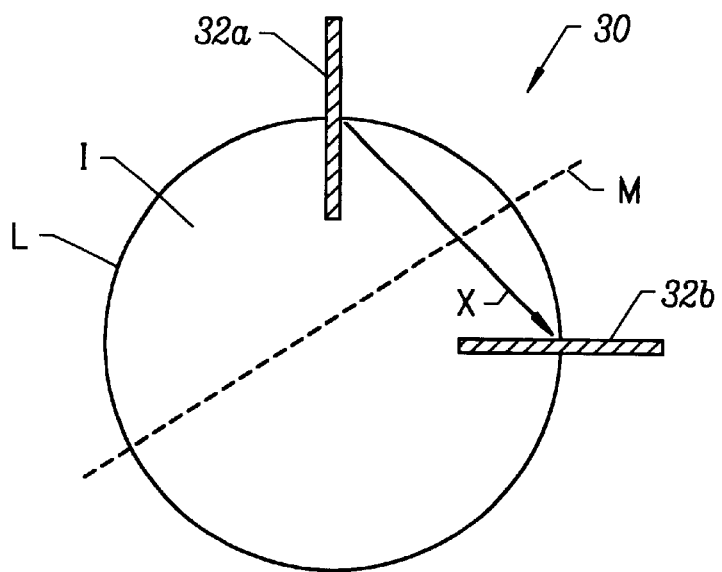
FIG. 4 schematically illustrates an alternative eye movement sensing system including two linear photodiode arrays, thereby providing absolute limbus location sensing as well as relative translation from the sum of linear array outputs.

Referring now to FIG. 4, an alternative sensing system 30 uses a pair of linear array photodiodes 32a, 32b. Such a linear array can give additional spacial information. Specifically, the digital nature of a linear array provides absolute edge location, rather than just relative measurements of the iris position. The accuracy of this absolute position sensing system will depend on the pixel dimensions of the linear array, as well as on classical optical constraints such as field of view, magnification, and the like.

The spacial information provided by linear arrays 32 is essentially the same as a single line of video. Advantageously, a single line pixel array avoids the limitations of standard video input, including the slow CCD refresh rates, and the like. This may provide sampling rates significantly higher than the typical video refresh rates of 30 or 60 Hz, and preferably as high or higher than high video refresh rates of about 120 Hz.

Currently available linear array photo diodes often include arrays of 256, 512, or 1,024 pixels. For a view field of 25 mm, the resolution of a 1,024 linear array photodiode is 24 µm. The dimension of each array element is about 2.5 µm wide by 25 µm long along the axis of the array, thereby providing quite good axial resolution. The wider dimension generally helps enhance sensitivity of the array.

Advantageously, the output from each element of linear arrays 32 can be summed to provide the same information available from a bulk detector, as described above. Therefore, so long as first array 32a and second array 32b cross limbus L at radially separated positions, the sum of the signals from these two linear arrays can be compared to determine the relative position of iris I along axis X between the arrays. In other words, in addition to the absolute edge position information provided by the array, pairs of linear photodiode arrays can be used as bulk photodetectors to measure the relative movement of iris I from a midline M bifurcating the arrays. Therefore, multiple pairs of arrays may be used in some applications.

The sensing and tracking systems of the present invention have generally been described with reference to movement along a single axis between pairs of detectors. As described with reference to FIG. 1, these systems will often include a second pair of detectors for sensing and/or tracking movements transverse to the sensing axis of the first pair. While such tracking may be enhanced by maintaining an orthogonal relationship between these two sensing axes, eyelids or other obstructions may be avoided by placing the pairs at oblique angles.

An alternative eye movement sensing system 40 is schematically illustrated in FIGS. 6 and 7. In this embodiment, eye E is imaged on to first and second digital linear photodetector arrays 42a, 42b, by first and second imaging optics 44a, 44b, respectively. The imaging optics, here illustrated schematically as a single lens, may optionally be disposed off the optical axis of the eye, with the optical paths of the imaging optics preferably being offset from each other by an angle 46 of about 90° relative to the optical axis of the eye. This allows each linear photodetector to independently sense movement in the X or Y orientation, as described above.

As illustrated in FIG. 7, the detector areas of the linear photodetectors 42a, 42b, receive light from the dark pupil, from the colored iris, and from the light sclera of eye E. In general, the detector areas receive light from two features of the eye defining a contrast border, with the linear detector preferably measuring light from along an axial segment extending beyond a first feature to a surrounding second feature on both ends. Where the first feature comprises a substantially circular structure of the eye such as a pupil and/or iris, movement of the eye along the axis of the axial segment may be analyzed by separating the signals from the individual sensors of the detector array into, for example, two sets, with the signals from one side of the array compared to signals to the other side of the array to determine movement of the eye as described hereinabove. Alternatively, the signals from the sensors along the array may be analyzed to determine the center of the relatively dark pupil and/or iris along the axial segment.

While the present invention has been described in some detail, by way of illustration and for clarity of understanding, a variety of changes, modifications, and adaptations will be obvious to those who skill in the art. For example, horizontal and vertical movements of the eye may be tracked by selectively comparing signals from three linear photodiodes, in which a processor treats each of the photodiodes as an element of two pairs. Hence, the scope of the present invention is limited solely by the appended claims.

What is claimed is:

1. A laser eye surgery system for effecting a desired change in optical characteristics of an eye during lateral movements of the eye in X and Y orientations, the eye having a first feature and a second feature with a contrast border therebetween, the system comprising:

a first linear photodetector having an elongate detector area, the detector area of the first linear photodetector oriented to receive light from the first and second feature of the eye along a first axis extending across the contrast border; and a second linear photodetector having an elongate detector area, the detector area of the second linear photodetector oriented to receive light from the first and second feature of the eye along a second axis extending across the contrast border, the second axis disposed at an angle relative to the first axis;

a processor coupled to the first and second linear photodetectors, the processor calculating the lateral movements of the eye in the X and Y orientations in response to the light received from along the first and second axes; and a laser coupled to the processor, the laser directing a laser beam toward the eye to effect the desired change in optical characteristics of the eye, the beam moving laterally in response to the calculated lateral movements of the eye.

2. The system of claim 1, wherein the elongate detector areas of the first and second linear detectors are substantially perpendicular.

3. The system of claim 1, wherein each linear detector produces a signal indicating total light within the elongate detector area.

4. The system of claim 1, wherein each linear detector comprises a linear array including a plurality of light sensors within the elongate detector area, each linear detector producing a signal indicating an alignment of the contrast border along the light sensors of the linear array.

5. The system of claim 1, further comprising first imaging optics and second imaging optics, the imaging optics in optical paths of the light from the eye, the first imaging optics imaging the light from along the first axis onto the first linear photodetector, the second imaging optics imaging the light from along the second axis onto the second linear photodetector.

6. The system of claim 5, wherein the optics image first and second axial segments of the eye onto the first and second linear photodetectors, respectively, and wherein the first and second axial segments cross.

7. The system of claim 6, wherein the axial segments cross within a pupil of the eye, the contrast border comprising at least one of the group comprising a limbus of the eye and a border between an iris and a pupil of the eye.

8. The system of claim 1, further comprising first and second beam scanning actuation systems coupled to the first and second linear detectors by the processor, respectively, each actuation system maintaining alignment between the linear detector and the eye along the axis of an associated linear detector.

9. A laser eye surgery method comprising:

illuminating a first feature and a second feature of an eye;

measuring light from the illuminated eye with a plurality of linear photodetectors while each linear detector is aligned to receive light from the first feature, from the second feature, and from across a contrast border therebetween;

determining lateral movements of the eye from the measured light;

directing a laser beam toward a corneal tissue of the eye to effect a desired change in optical characteristics of the eye; and moving the beam laterally in response to the lateral movements of the eye.

10. The laser eye surgery method of claim 9, further comprising imaging the light from the illuminated eye so that first and second axial segments of the eye are imaged onto the first and second linear photodetectors, respectively, wherein the first and second axial segments cross within a pupil of the eye.

* * * * *